(12) United States Patent
Bannigan

(10) Patent No.: US 9,795,493 B1
(45) Date of Patent: Oct. 24, 2017

(54) EXPANDABLE INTERVERTEBRAL IMPLANT AND METHODS OF USE THEREOF

(71) Applicant: NuVasive, Inc., San Diego, CA (US)

(72) Inventor: Shaeffer Bannigan, San Diego, CA (US)

(73) Assignee: NUVASIVE, INC., San Diego, CA (US)

( * ) Notice: Subject to any disclaimer, the term of this patent is extended or adjusted under 35 U.S.C. 154(b) by 134 days.

(21) Appl. No.: 14/217,358

(22) Filed: Mar. 17, 2014

Related U.S. Application Data

(60) Provisional application No. 61/789,912, filed on Mar. 15, 2013.

(51) Int. Cl.
*A61F 2/44* (2006.01)
*A61F 2/30* (2006.01)

(52) U.S. Cl.
CPC .... *A61F 2/447* (2013.01); *A61F 2002/30601* (2013.01)

(58) Field of Classification Search
CPC ............................ A61F 2/44; A61F 2002/4415
USPC .............................................. 623/17.11–17.16
See application file for complete search history.

(56) References Cited

U.S. PATENT DOCUMENTS

| | | | |
|---|---|---|---|
| 5,596,325 A | 1/1997 | Maas | |
| 5,972,015 A | 10/1999 | Scribner | |
| 6,193,757 B1 | 2/2001 | Foley | |
| 7,854,766 B2 | 12/2010 | Moskowitz | |
| 7,951,199 B2 | 5/2011 | Miller | |
| 8,109,972 B2* | 2/2012 | Zucherman | A61B 17/7065 606/249 |
| 2002/0026197 A1 | 2/2002 | Foley | |
| 2002/0151976 A1 | 10/2002 | Foley | |
| 2004/0088054 A1 | 5/2004 | Berry | |
| 2004/0102774 A1 | 5/2004 | Trieu | |
| 2004/0133280 A1 | 7/2004 | Trieu | |
| 2004/0199168 A1 | 10/2004 | Bertagnoli | |
| 2005/0043800 A1 | 2/2005 | Paul | |
| 2005/0113920 A1 | 5/2005 | Foley | |
| 2005/0174744 A1 | 8/2005 | Zheng | |
| 2005/0182417 A1 | 8/2005 | Pagano | |
| 2005/0256576 A1 | 11/2005 | Moskowitz | |
| 2005/0261683 A1* | 11/2005 | Veldhuizen | A61F 2/44 623/17.11 |

(Continued)

FOREIGN PATENT DOCUMENTS

| | | |
|---|---|---|
| CA | 2649107 | 10/2007 |
| EP | 2526882 | 11/2012 |

(Continued)

*Primary Examiner* — Christopher Beccia
(74) *Attorney, Agent, or Firm* — Rory Schermerhorn; Jennifer Russell

(57) ABSTRACT

An expandable intervertebral implant including a first wall comprised of a male portion and a female portion in telescoping engagement with each other and a second wall comprised of a plurality of links, wherein the first wall and second wall are coupled to each other by hinges at each of the leading and trailing ends of the implant. The expandable implant is configured to be inserted into a disc space in a collapsed, narrow profile configuration and then unilaterally expanded in an anterior or posterior direction to a fully expanded, larger foot print configuration.

5 Claims, 13 Drawing Sheets

(56) References Cited

U.S. PATENT DOCUMENTS

| | | |
|---|---|---|
| 2006/0036241 A1 | 2/2006 | Siegal |
| 2006/0074488 A1 | 4/2006 | Abdou |
| 2006/0078428 A1 | 4/2006 | Zheng |
| 2006/0142858 A1 | 6/2006 | Colleran |
| 2006/0241643 A1 | 10/2006 | Lim |
| 2007/0010845 A1 | 1/2007 | Gong |
| 2007/0067034 A1 | 3/2007 | Chirico |
| 2007/0073398 A1 | 3/2007 | Fabian |
| 2007/0118222 A1 | 5/2007 | Lang |
| 2007/0260314 A1 | 11/2007 | Biyani |
| 2007/0282449 A1 | 12/2007 | De Villiers |
| 2008/0082173 A1* | 4/2008 | Delurio .............. A61F 2/4465 623/17.16 |
| 2008/0208255 A1 | 8/2008 | Siegal |
| 2008/0243251 A1 | 10/2008 | Stad |
| 2008/0243255 A1 | 10/2008 | Butler |
| 2008/0281346 A1 | 11/2008 | Greenhalgh |
| 2009/0076607 A1 | 3/2009 | Aalsma |
| 2009/0152061 A1* | 6/2009 | Tsai .................. B60T 11/16 188/344 |
| 2009/0157084 A1 | 6/2009 | Aalsma |
| 2009/0216331 A1 | 8/2009 | Grotz |
| 2009/0234454 A1 | 9/2009 | Siegal |
| 2009/0248092 A1 | 10/2009 | Bellas |
| 2009/0281628 A1 | 11/2009 | Oglaza |
| 2010/0010633 A1 | 1/2010 | Kohm |
| 2010/0161062 A1 | 6/2010 | Foley |
| 2010/0174373 A1 | 7/2010 | Galley |
| 2010/0198263 A1 | 8/2010 | Siegal |
| 2010/0262147 A1 | 10/2010 | Siegal |
| 2010/0286779 A1 | 11/2010 | Thibodeau |
| 2010/0286783 A1 | 11/2010 | Lechmann |
| 2010/0292799 A1 | 11/2010 | Hansell |
| 2010/0292801 A1 | 11/2010 | Hansell |
| 2011/0093072 A1 | 4/2011 | Siegal |
| 2011/0125270 A1 | 5/2011 | Paul |
| 2011/0184515 A1 | 7/2011 | Siegal |
| 2011/0251689 A1 | 10/2011 | Seifert |
| 2011/0288646 A1 | 11/2011 | Moskowitz |
| 2011/0301712 A1 | 12/2011 | Palmatier |
| 2012/0004732 A1 | 1/2012 | Goel |
| 2012/0071977 A1 | 3/2012 | Oglaza |
| 2012/0083887 A1 | 4/2012 | Purcell |
| 2012/0209386 A1 | 8/2012 | Triplett |
| 2012/0215313 A1 | 8/2012 | Saidha |
| 2012/0215316 A1 | 8/2012 | Mohr |
| 2012/0259416 A1 | 10/2012 | Blackwell |
| 2012/0271422 A1 | 10/2012 | Miller |
| 2012/0290094 A1 | 11/2012 | Lim |
| 2012/0296433 A1 | 11/2012 | Farin |
| 2012/0310048 A1 | 12/2012 | Siegal |
| 2012/0310350 A1 | 12/2012 | Farris |
| 2013/0035762 A1 | 2/2013 | Siegal |
| 2013/0041471 A1* | 2/2013 | Siegal .............. A61F 2/442 623/17.16 |
| 2013/0079883 A1* | 3/2013 | Butler .............. A61F 2/4425 623/17.16 |
| 2013/0103156 A1 | 4/2013 | Packer |
| 2013/0110239 A1 | 5/2013 | Siegal |
| 2013/0123924 A1 | 5/2013 | Butler |
| 2013/0158664 A1* | 6/2013 | Palmatier .......... A61F 2/447 623/17.16 |
| 2013/0158668 A1 | 6/2013 | Nichols |
| 2013/0166031 A1 | 6/2013 | Caratsch |
| 2013/0190876 A1 | 7/2013 | Drochner |
| 2013/0274883 A1 | 10/2013 | Mcluen |
| 2014/0031940 A1 | 1/2014 | Banouskou |

FOREIGN PATENT DOCUMENTS

| | | |
|---|---|---|
| WO | WO-2007008568 | 1/2007 |
| WO | WO-2012115631 | 8/2012 |
| WO | WO-2013006669 | 1/2013 |

* cited by examiner

EXPANDABLE INTERVERTEBRAL IMPLANT AND METHODS OF USE THEREOF

CROSS REFERENCE TO RELATED APPLICATIONS

This application claims the benefit of the filing date of U.S. Provisional Application No. 61/789,912, which was filed on Mar. 15, 2013. The contents of U.S. Application No. 61/789,912 are incorporated by reference in their entirety as a part of this application.

BACKGROUND

The present application relates to spinal fusion surgery, and more particularly, to an expandable intervertebral implant device.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein.

DETAILED DESCRIPTION

Figure 1:
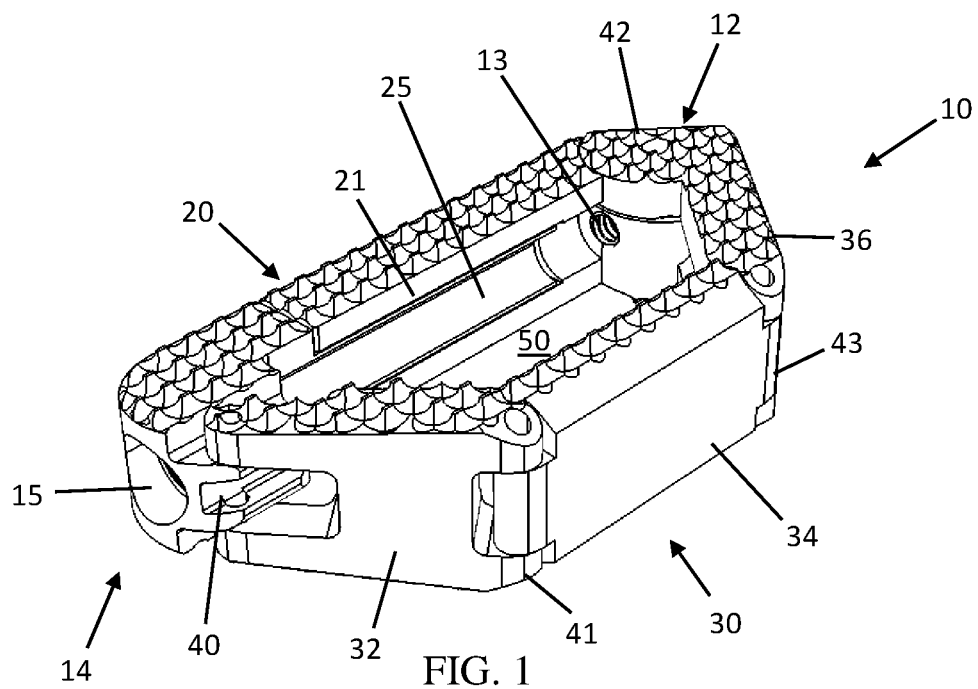
FIG. 1 is a perspective view of an exemplary embodiment of an expandable intervertebral implant in its fully expanded state.

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The expandable intervertebral implant disclosed herein boasts a variety of inventive features and components that warrant patent protection, both individually and in combination.

FIGS. 1-7 illustrate an exemplary embodiment of an expandable intervertebral implant 10. The expandable intervertebral implant 10 includes a telescoping posterior wall 20 and an anterior wall 30. The posterior 20 and anterior 30 walls are connected by a hinge 40, 42 at the each of the leading end 12 and trailing end 14, respectively. The expandable intervertebral implant 10 has a length from the leading end 12 to the trailing end 14 dimensioned to span the width of the intervertebral disc space when the implant 10 is in its fully expanded state, i.e. the fully expanded implant is long enough, from leading end 12 to trailing end 14, to extend from the distal cortical bone lateral aspect to the proximal cortical bone lateral aspect of the vertebral bodies adjacent the disc space.

The implant comprises a telescoping posterior wall 20, formed of male 22 and female portions 24 and an anterior wall 30 formed of a plurality of links 32, 34, 46 coupled to each other and to the posterior wall 20 by a plurality of hinges 40, 42. The implant 10 is configured to be inserted into the intervertebral disc space via a lateral approach to the spine in its collapsed insertion state. In its collapsed state, the linked anterior wall 30 and the telescoping posterior wall 20 are generally parallel to each other in generally straight, linear configurations, respectively. In the collapsed state, the medial faces 21, 31 of the posterior wall 20 and anterior wall 30 are in close proximity to each other. According to the embodiment shown in FIG. 1, once the implant 10 is placed in the desired position within the disc space in its collapsed state, the implant 10 is expanded to the expanded state shown in FIG. 1 by displacing the anterior wall 30 anteriorly while the posterior wall 20 remains in a fixed position. According to this exemplary embodiment, an insertion tool (not shown) is used to position the implant 10 within the disc space and subsequently expand the implant 10. The insertion tool has a distal tip that engages the insertion tool aperture 13 on the medial face 21 of the leading end of the anterior wall 20. Grooves 25, 35 along a substantial portion of the medial faces 21, 31 of the anterior and posterior wall form a channel to accommodate the shaft of the insertion tool during insertion of the implant 10. The insertion tool is used to push the proximal end 14 of the implant 10 toward the distal end 12, causing the telescoping posterior wall 20 to decrease in length and the links 32, 34, 36 of the anterior wall 30 to pivot about the hinges 40, 41, 42, 43, thereby causing the width (i.e. the anterior to posterior dimension of the implant) to expand. Upon expansion, the implant 10 comprises a fusion aperture 50 bordered by the anterior 30 and posterior walls 20.

Figure 2:
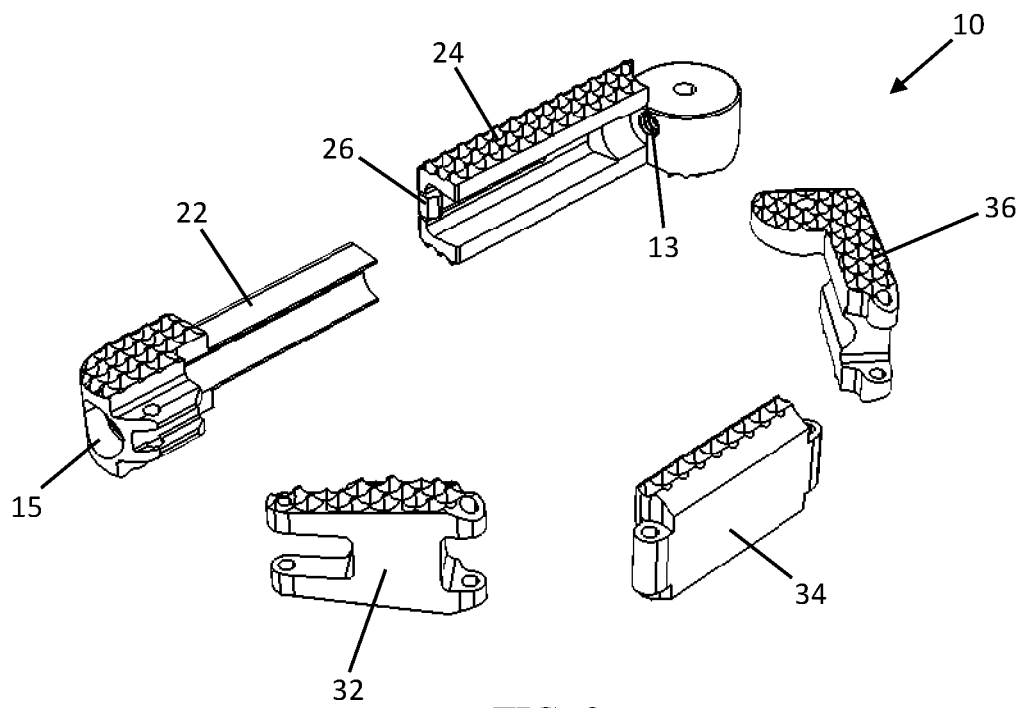
FIG. 2 is an exploded perspective view of the expandable intervertebral implant according to the exemplary embodiment of FIG. 1.
Figure 3:
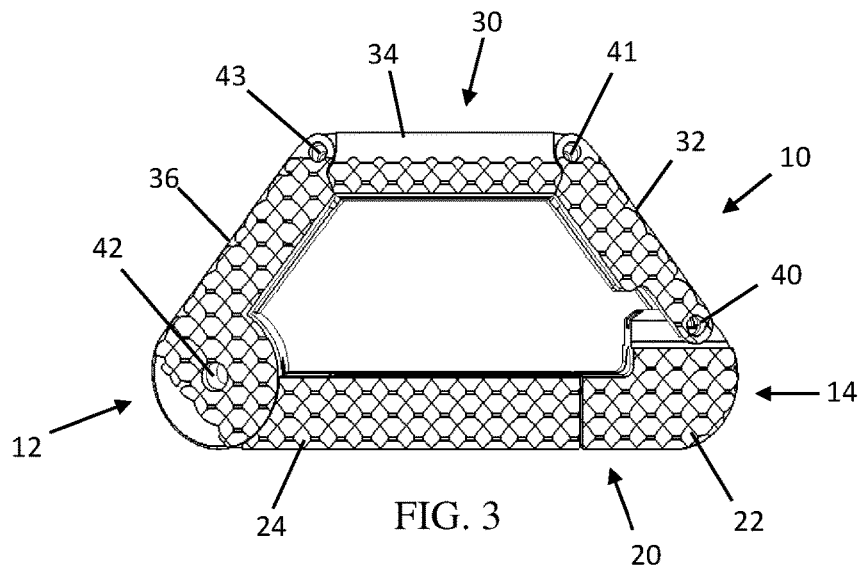
FIG. 3 is a top view of the of the expandable intervertebral implant according to the exemplary embodiment of FIG. 1.

FIG. 2 is an exploded perspective view of the expandable implant 10. The telescoping posterior wall 20 has a leading end 12 and a trailing end 14, and further includes a distal female portion 24 and a proximal male portion 22. The medial face 21 of the leading end 12 of the posterior wall 20 includes an aperture 13 for receiving the distal tip of an insertion tool (not shown). The proximal most end of the female portion 24 includes a mating feature 27 that complements a mating feature 26 at the distal most of the male portion 22 such that when the implant is fully expanded, the mating features 26, 27 engage to lock the implant 10 in the expanded state. The medial faces 21 of the male and female portions 22, 24 of the posterior wall 20 include a groove 25 to accommodate the shaft of the insertion tool. The trailing end 14 of the posterior wall 20 includes an insertion tool aperture 15 to receive the shaft of the insertion tool. The top and bottom surfaces 29, 39 of the posterior wall 20 are bone contacting surfaces that include anti-migration features 70. The anterior wall 30 includes a plurality of links 32, 34, 36. The links 32, 34, 36 are configured to form a hinge 40, 41, 42, 43 at each end of the link 32, 34, 36. The distal most link 36 forms a hinge with the distal end of the posterior wall 20 and the proximal most link 32 forms a hinge 40 with the proximal end 14 of the posterior wall 20. According to the embodiment shown in FIGS. 1 and 2, the anterior wall 30 further comprises a middle link 34 hingedly coupled to the distal most link 36 and the proximal most link 32. The anterior wall 30 has top and bottom surfaces 29, 39 that are bone contacting surfaces including anti-migration features 70.

Figure 4:
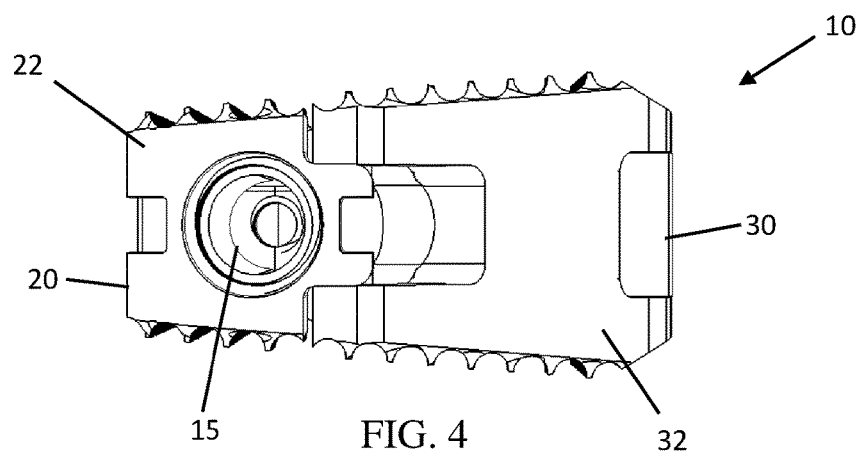
FIG. 4 is a lateral view of the trailing end of the expandable intervertebral implant according to the exemplary embodiment of FIG. 1.
Figure 5:
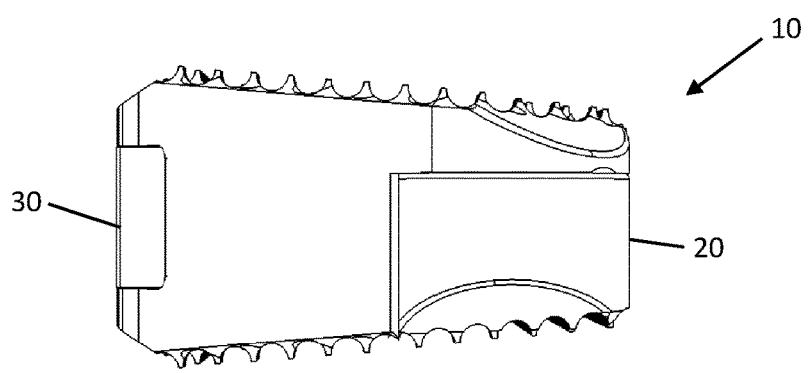
FIG. 5 is lateral view of the leading end of the expandable intervertebral implant according to the exemplary embodiment of FIG. 1.
Figure 6:
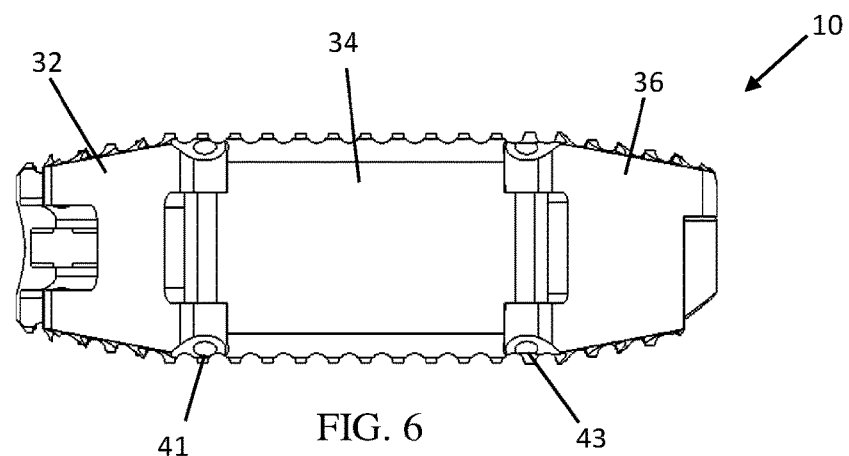
FIG. 6 is an anterior view of the expandable intervertebral implant according to the exemplary embodiment of FIG. 1.
Figure 7:
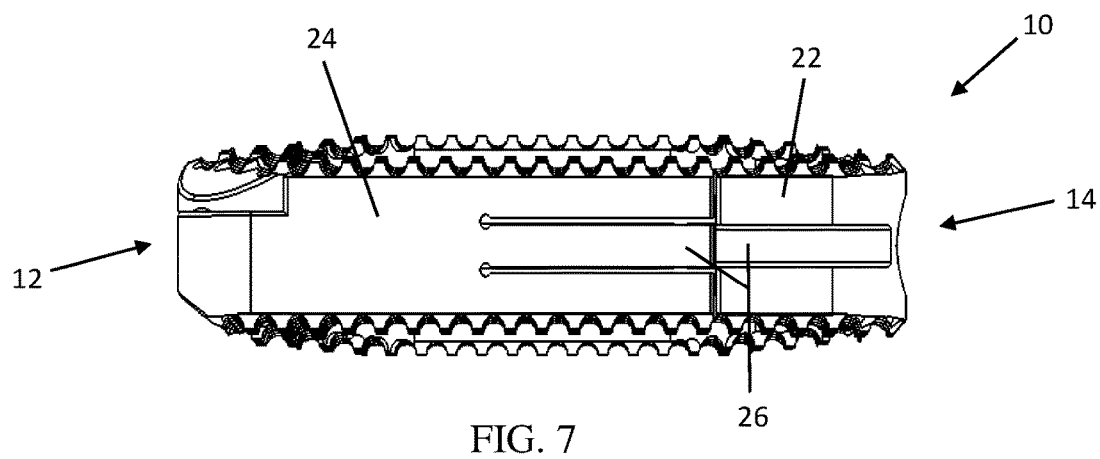
FIG. 7 is a posterior view of the expandable intervertebral implant according to the exemplary embodiment of FIG. 1.

As seen in FIGS. 4 and 5, according to this exemplary embodiment, the anterior wall 30 has a greater height than the posterior wall 20 to restore lordosis at the treated spinal level. Also demonstrated in FIGS. 4 and 5, the anti-migration features 70 on the top and bottom surfaces 29, 39 of the implant 10 according to this embodiment included a plurality of teeth. As best seen in FIG. 6, the middle link 34 may have a uniform height and the links 32, 36 connecting the posterior wall to the middle link change in height along the length of the link. As best seen in FIG. 7, according to this exemplary embodiment, the mating feature 27 on the female portion 24 of the posterior wall 20 is a deflectable tab that mates with a complementary recess 28 on the male portion 24 of the posterior wall 20.

Figure 8:
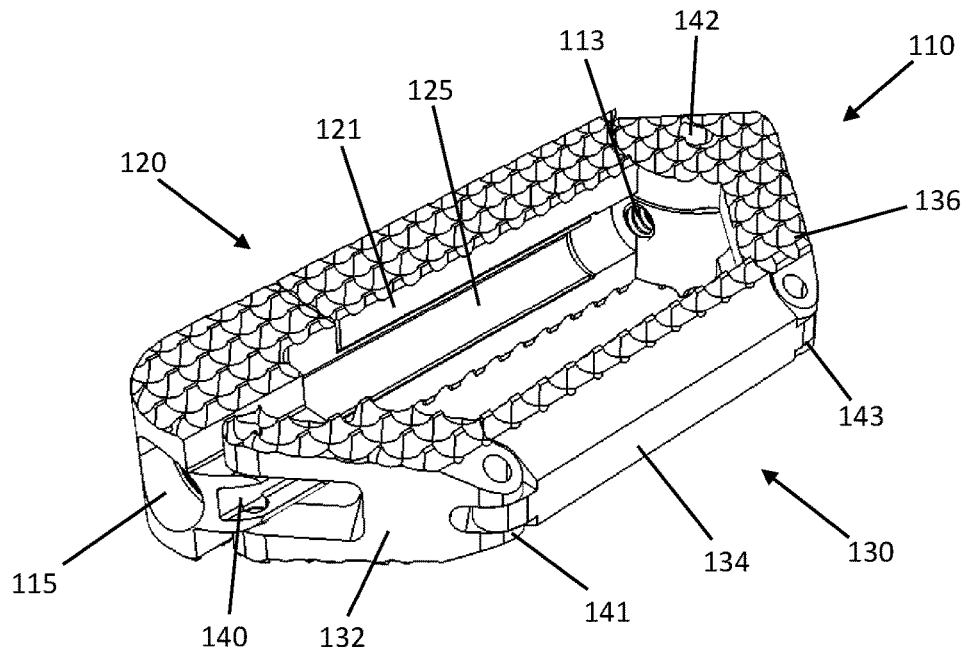
FIG. 8 is a perspective view of an alternative embodiment of an expandable intervertebral implant in its fully expanded state.
Figure 9:
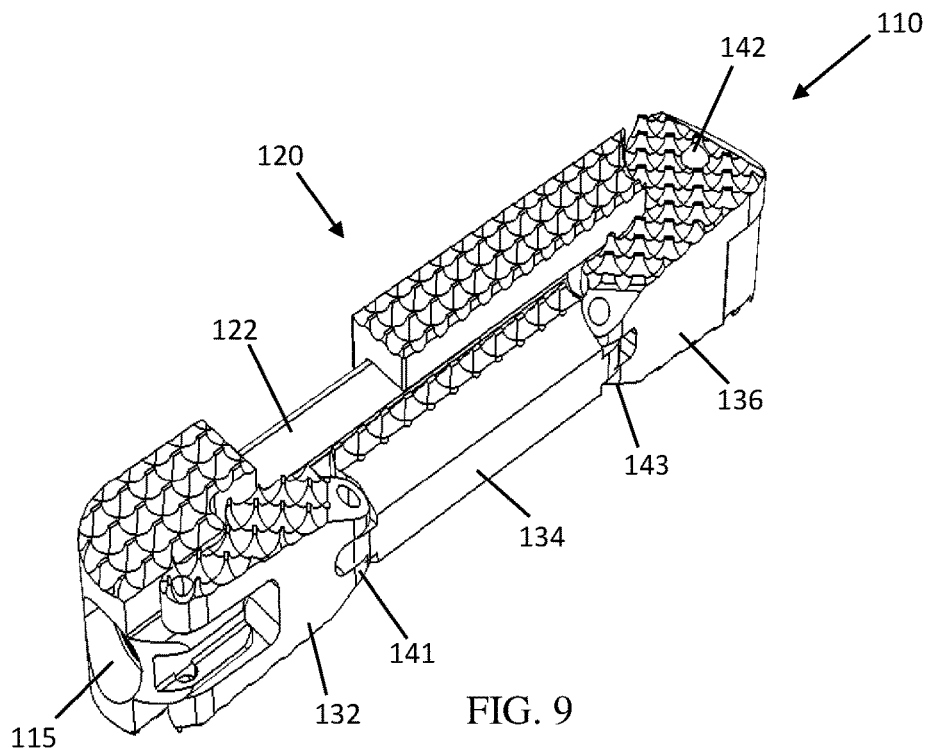
FIG. 9 is a perspective view of the alternative embodiment of the expandable intervertebral implant of FIG. 8 in its collapsed state.
Figure 10:
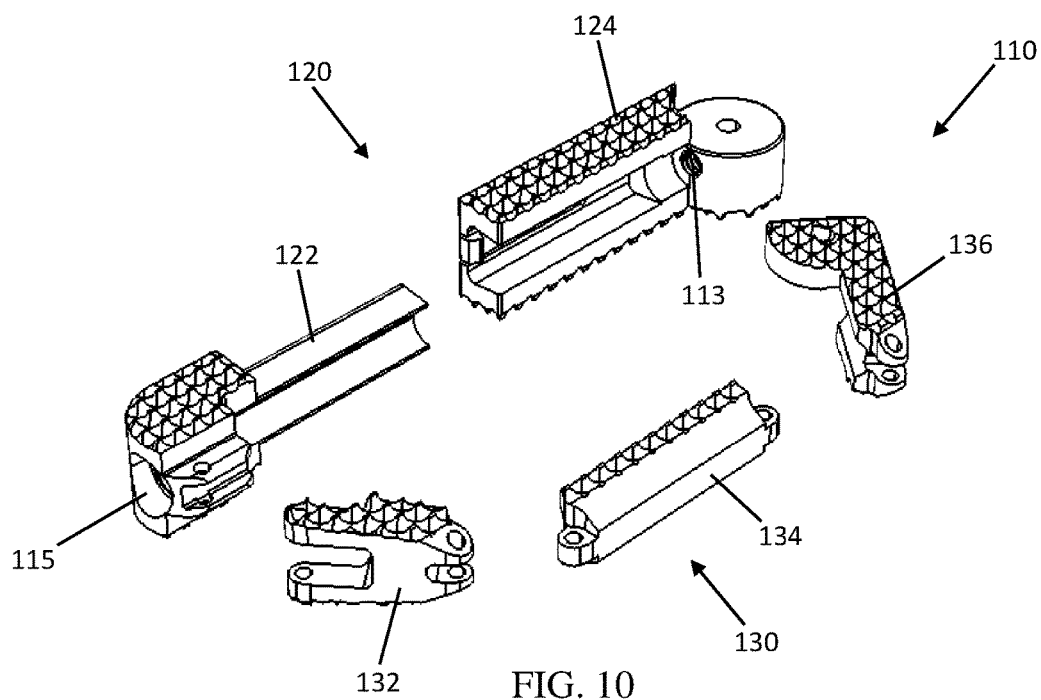
FIG. 10 is an exploded perspective view of the alternative embodiment of the expandable intervertebral implant of FIG. 8.
Figure 11:
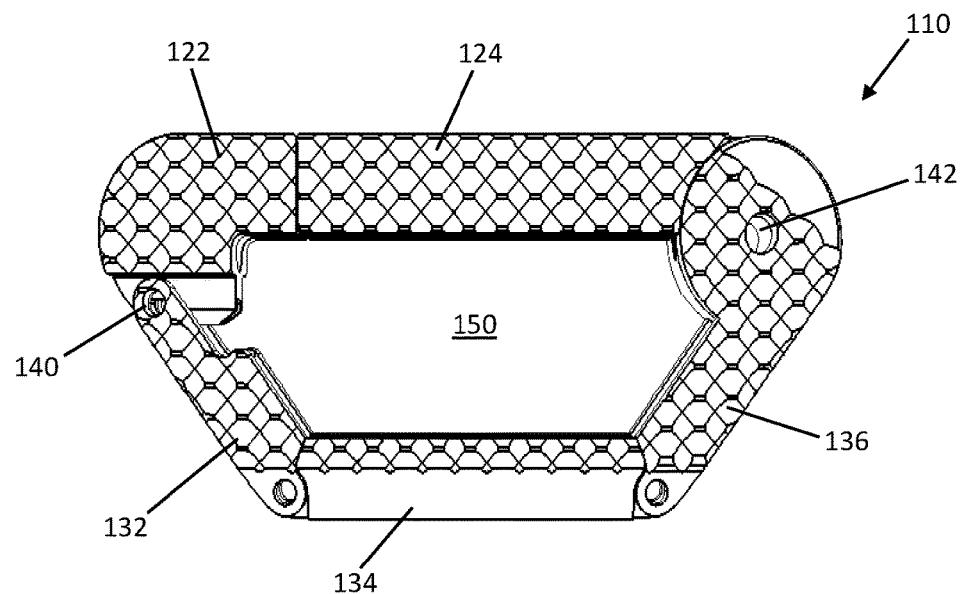
FIG. 11 is a top view of the expandable intervertebral implant of FIG. 8 in its fully expanded state.
Figure 12:
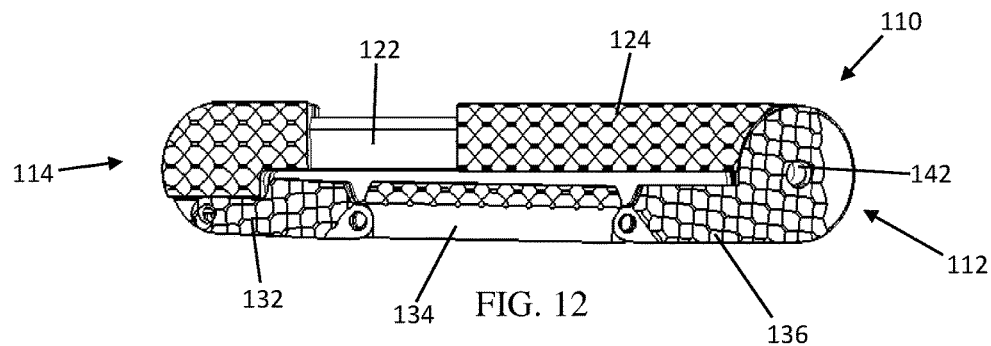
FIG. 12 is a top view of the expandable intervertebral implant of FIG. 8 in its collapsed state.
Figure 13:
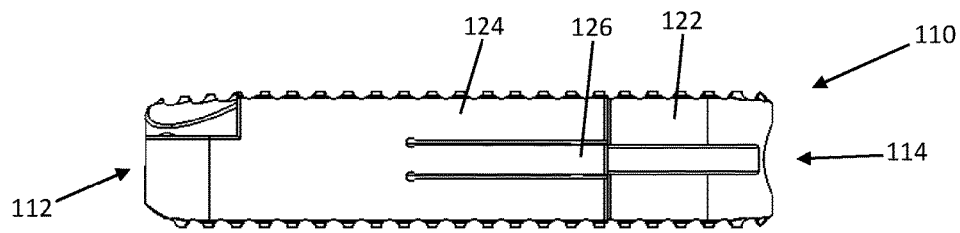
FIG. 13 is an anterior view of the expandable intervertebral implant of FIG. 8.
Figure 14:
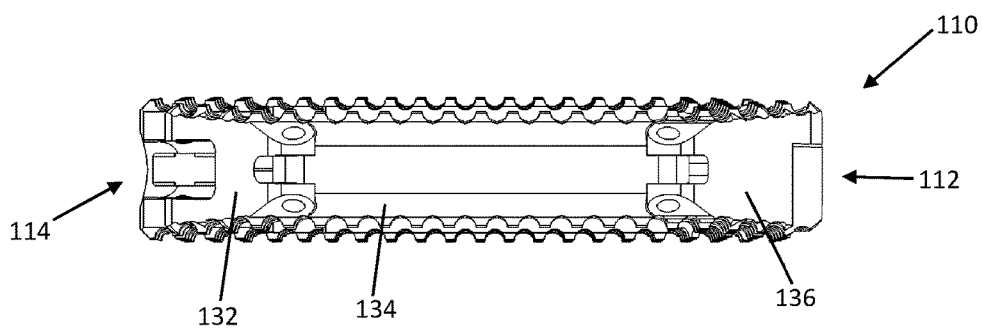
FIG. 14 is a posterior view of the expandable intervertebral implant of FIG. 8.
Figure 15:
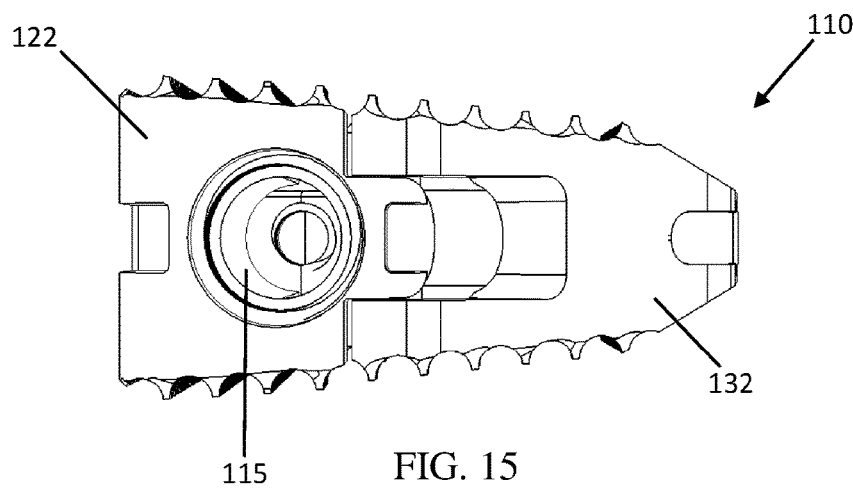
FIG. 15 is a lateral view of the leading end of the expandable intervertebral implant of FIG. 8.
Figure 16:
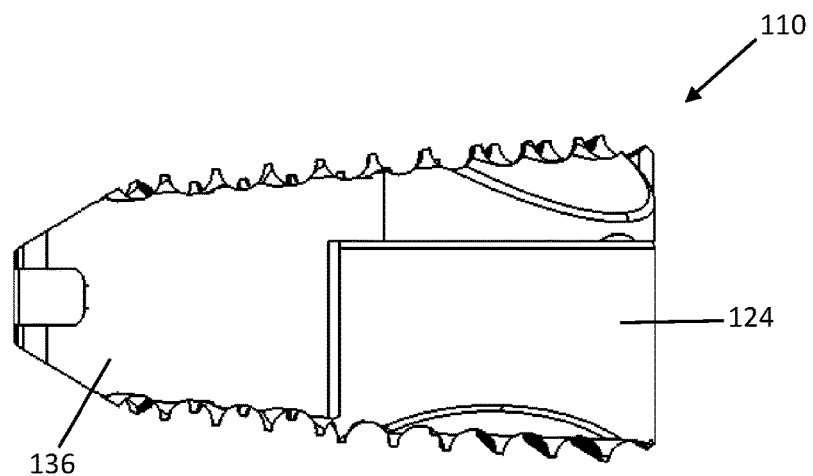
FIG. 16 is a lateral view of the trailing end of the expandable intervertebral implant of FIG. 8.
Figure 17:
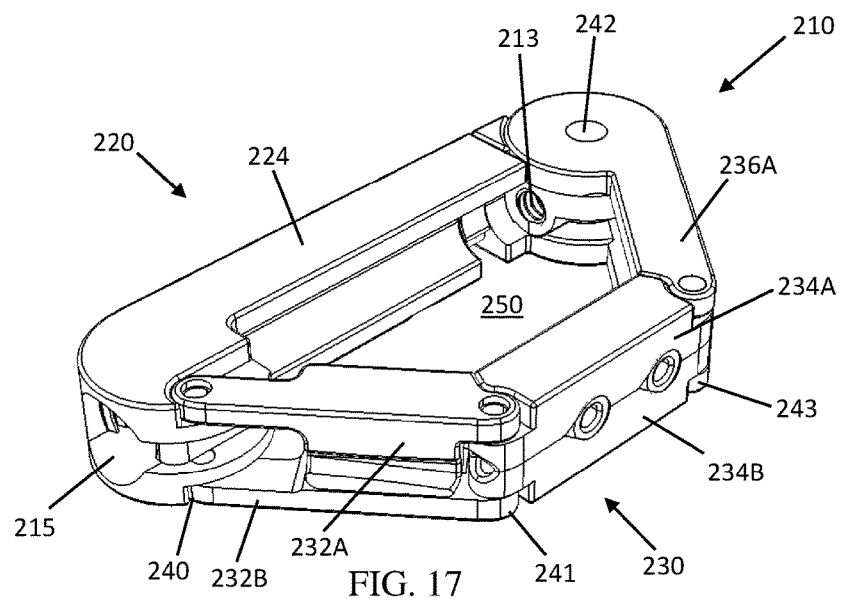
FIG. 17 is a perspective view of another alternative embodiment of an expandable intervertebral implant in its collapsed state.
Figure 18:
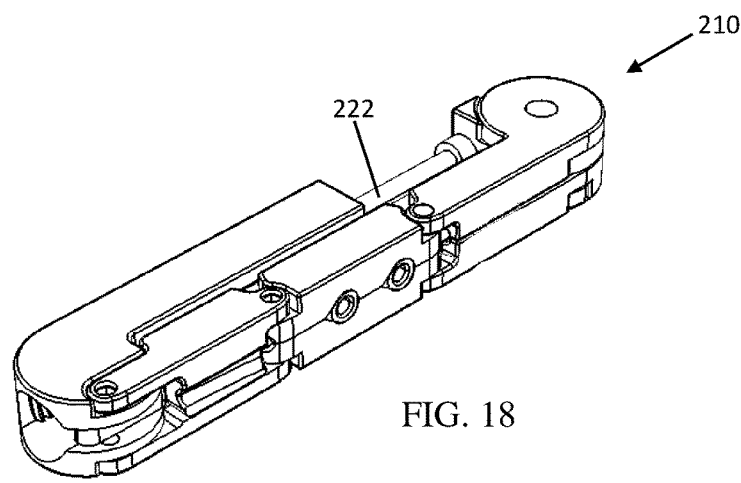
FIG. 18 is an anterior view of the expandable intervertebral implant of FIG. 17.
Figure 19:
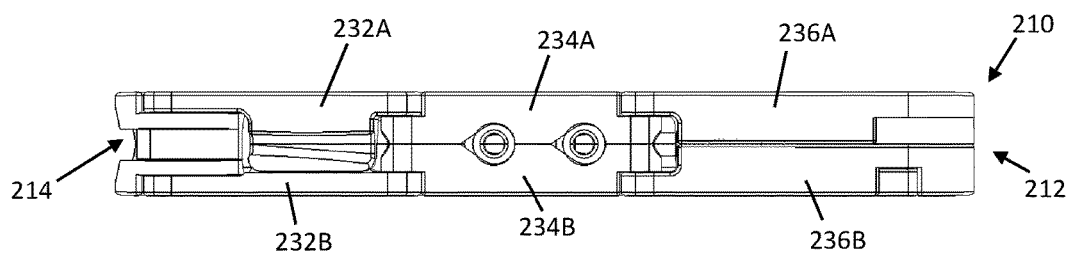
FIG. 19 is a perspective view of the expandable intervertebral implant of FIG. 17 in its anteriorly expanded.

FIGS. 8-16 illustrate an alternative embodiment of an expandable intervertebral implant 110. This alternative embodiment has all the same features and components described above for the exemplary embodiment of FIGS. 1-7, except that this alternative embodiment is configured to be inserted into an anterior portion of the disc space and then expanded in a posterior direction by displacing the posterior wall 130. As such, the anterior wall 120 is formed of a female portion 124 and the male portion 122 engaged in a telescoping relationship with each other. As seen in FIGS. 8 and 9, the length of the overall anterior wall 120 is greater (and, consequently, the implant) when the implant 110 is in the collapsed insertion state than when the implant 110 is in the full expanded state. According to this alternative embodiment, the posterior wall 130 includes a plurality of hinged links 132, 134, 136.

As can be seen from FIGS. 13-16, the anterior wall 120 of the implant 110 has a greater height than the posterior wall 130. The middle link 134 of the posterior wall 130 has a uniform height, and the links 132, 136 flanking the middle link 134 decrease in height from the hinge 140, 142 with the anterior wall 120 to the hinge with the middle link 141, 143.

FIGS. 24-28 illustrate another alternative embodiment of an expandable intervertebral implant 310. The implant 310 according to this embodiment has the same components as described above for the embodiment shown in FIGS. 8-16. As described above for the previous embodiment, the expandable vertebral implant 310 has a telescoping anterior wall 320 formed of a male portion 322 and a female portion 324 in sliding engagement with each other. The telescoping anterior wall 320 includes a locking mechanism 326, 327 to lock the male and female portions 322, 324 in place with respect to each other when the implant 310 has been expanded to its fully expanded configuration. The telescoping anterior wall 320 is coupled to a posterior wall 330 by a hinge 340, 342 at each of the leading and trailing ends 312, 314 of the implant 310, respectively. The posterior wall 330 is comprised of a plurality of links 332, 334, 336 that are connected at hinges 340, 341, 342, 343 to allow the footprint of the implant to be expanded when the trailing end 314 of the anterior wall 320 is pushed toward the leading end 312 of the anterior wall 320. The decrease in length of the anterior wall causes the posterior wall 330 to bend at the hinges 340, 341, 342, 343 and allows the footprint of the intervertebral implant 310 to expand posteriorly. While the embodiment shown in FIGS. 24-28 has the same general structure of the implant 110 of FIGS. 8-16, the implant 310 of FIGS. 24-28 further includes a recessed portion 328 on the top 329 and/or bottom surface 339 of the anterior wall 320. The recessed portion 328 is located at the center portion of the length of the anterior wall 320 when the implant 310 is in its fully expanded configuration (i.e. when the male portion 322 and female portion 324 are engaged and locked). The recessed portion 328 can be used as a marker for the surgeon using fluoroscopy or other radiographic techniques to determine proper placement of the expandable intervertebral implant 310 within the disc space during the procedure or to confirm proper placement of the implant post operatively.

FIGS. 17-23 demonstrate another embodiment of an expandable intervertebral implant 210. The implant 210 according to this embodiment is unilaterally expandable in the anterior/posterior direction and the anterior wall 230 is also expandable in the cranial/caudal direction in order to restore lordosis at the spinal level being treated. The implant 210 according to the this embodiment includes the same features and components as the previously described embodiments. For example, the implant includes a telescoping posterior wall 220 formed of a male portion 222 that is received within a female portion 224. The anterior wall 230 is formed of a plurality of links 232, 234, 236. The method of anterior expansion according to this embodiment works the same way as previously described for the first and second embodiments of FIGS. 1-7 and 8-16, respectively. As demonstrated by FIGS. 17-19, the implant 210 is inserted into the disc space in its narrow profile collapsed insertion state, then the proximal end 214 of the implant 210 is urged toward the distal end 212, causing the telescoping posterior wall 220 to decrease in length and thereby causing the linked anterior wall 230 to bend at the hinges 240, 241, 242, 243 as it expands anteriorly.

Figure 20:
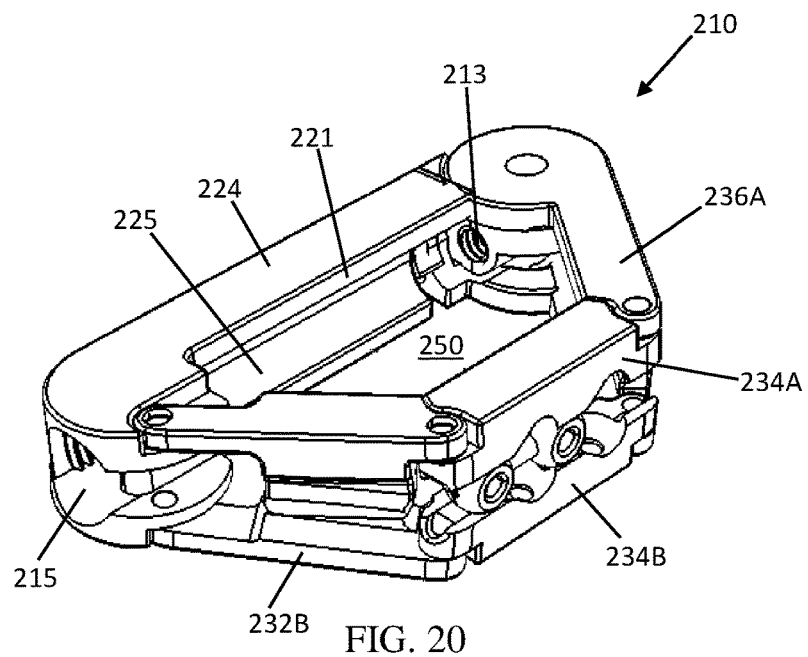
FIG. 20 is a perspective view of the expandable intervertebral implant of FIG. 17 in its fully expanded state.
Figure 21:
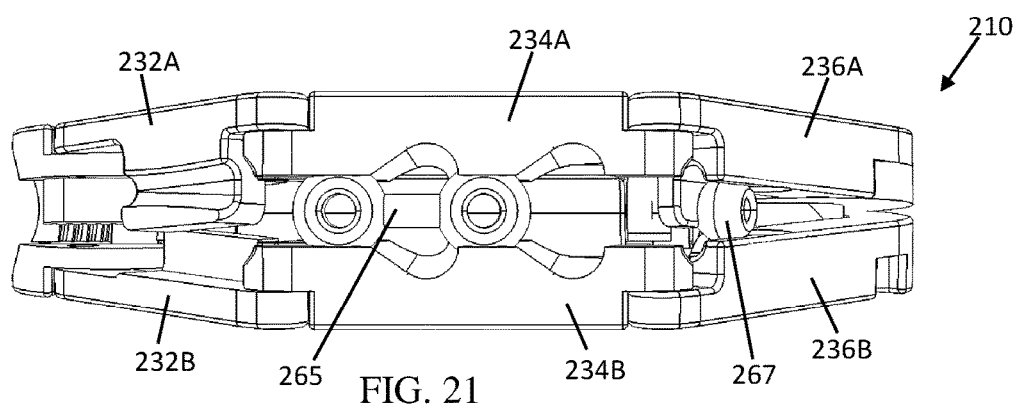
FIG. 21 is an anterior view of the expandable intervertebral implant of FIG. 17 in its fully expanded state.
Figure 22:
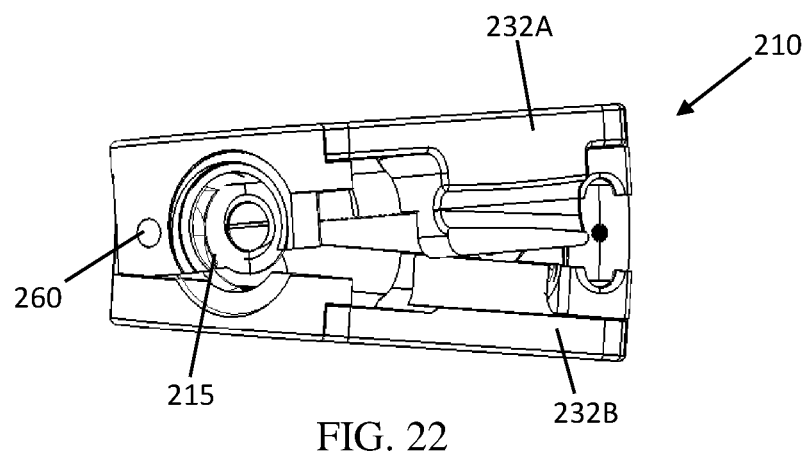
FIG. 22 is a lateral view of the trailing end of the expandable intervertebral implant of FIG. 17 in its fully expanded state.
Figure 23:
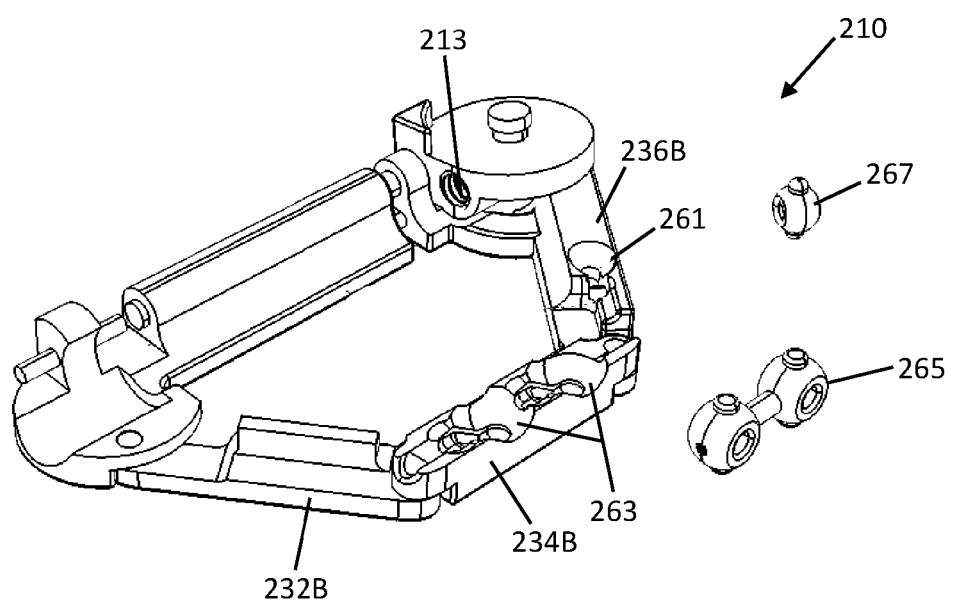
FIG. 23 is a partially exploded perspective view of the expandable intervertebral implant of FIG. 17
Figure 24:
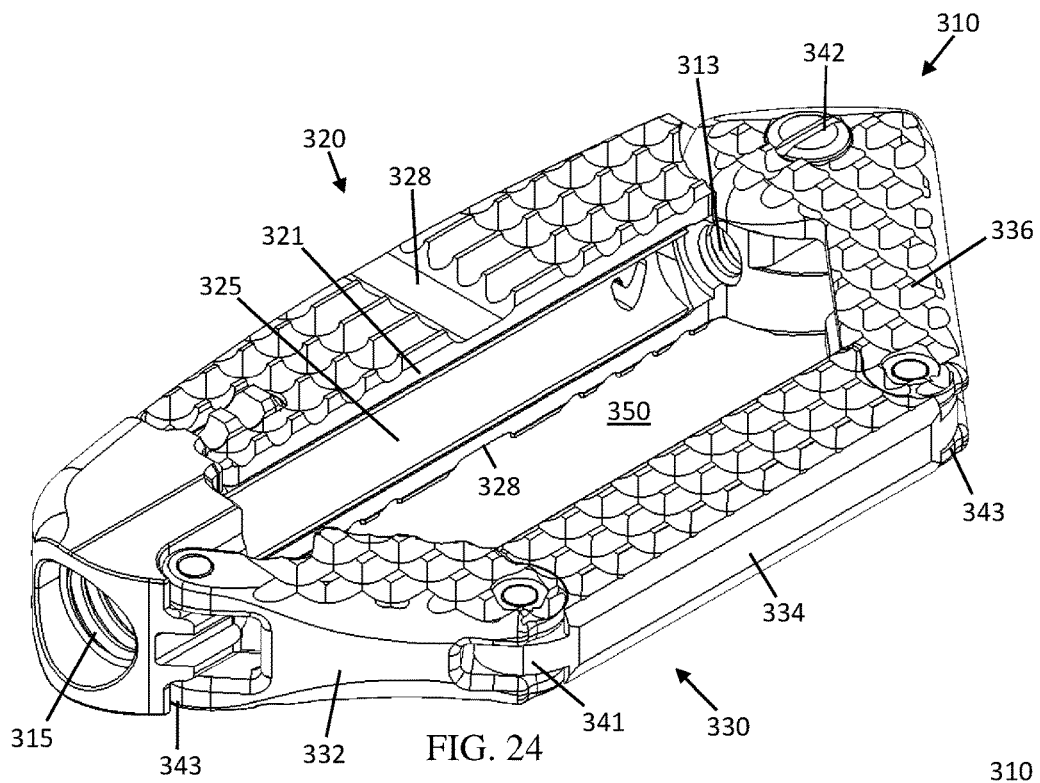
FIG. 24 is a perspective view of yet another alternative embodiment of an expandable intervertebral implant in its fully expanded state.
Figure 25:
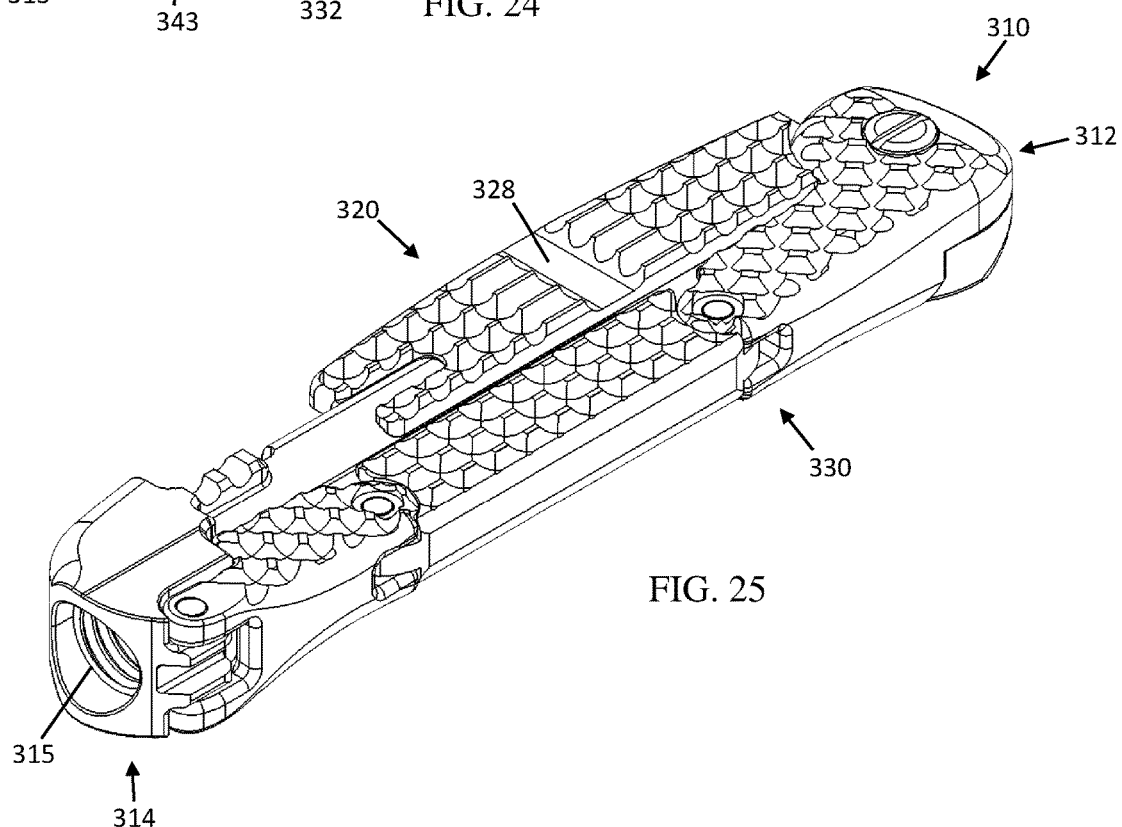
FIG. 25 is a perspective view of the expandable intervertebral implant of FIG. 24 in its collapsed state.
Figure 26:
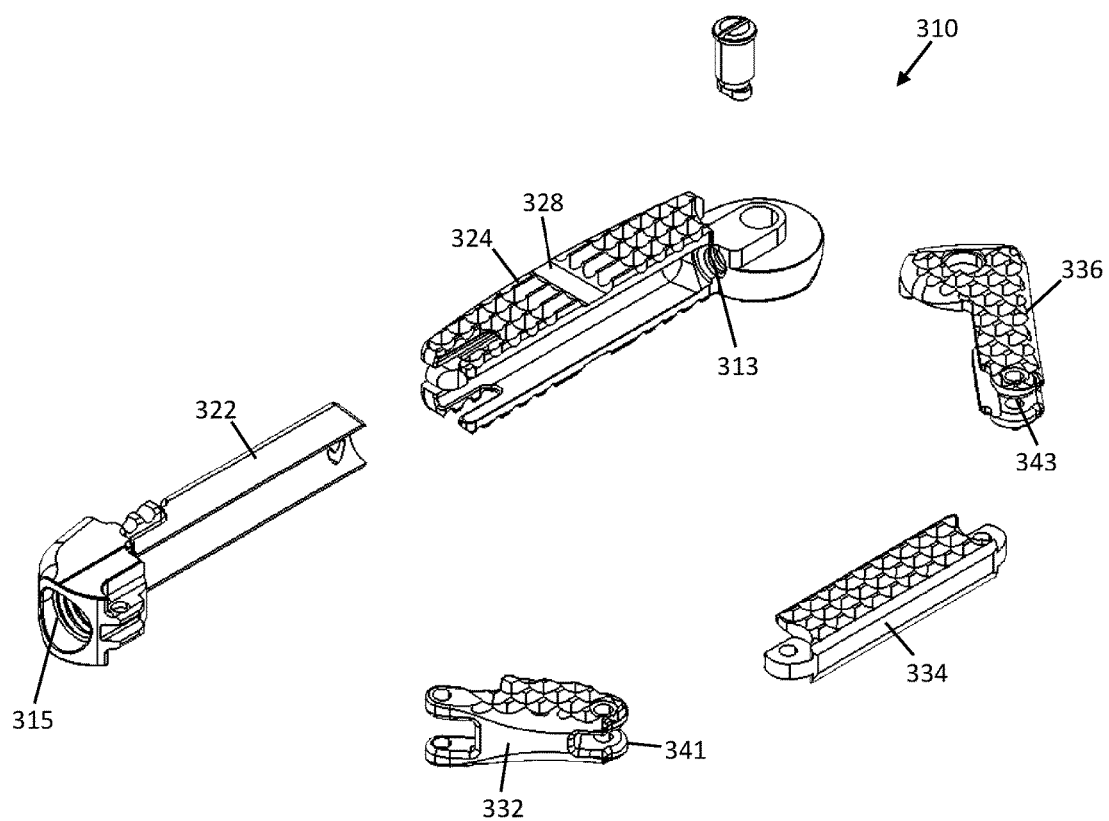
FIG. 26 is an exploded perspective view of the expandable intervertebral implant of FIG. 24.
Figure 27:
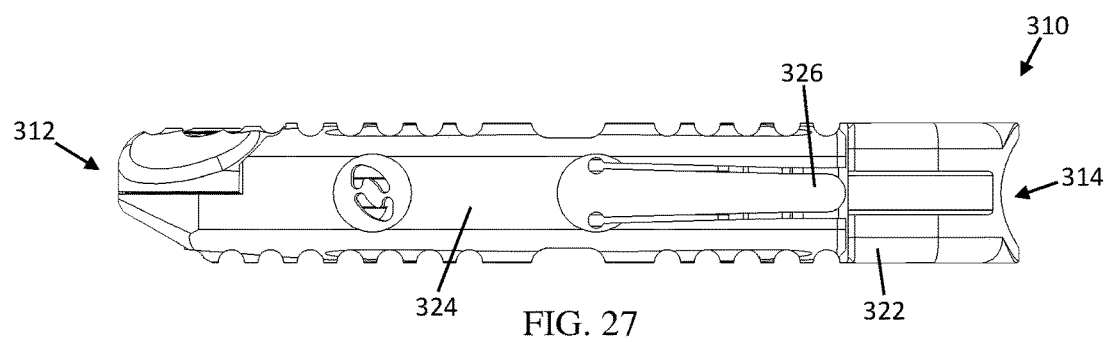
FIG. 27 is an anterior view of the expandable intervertebral implant of FIG. 24.
Figure 28:
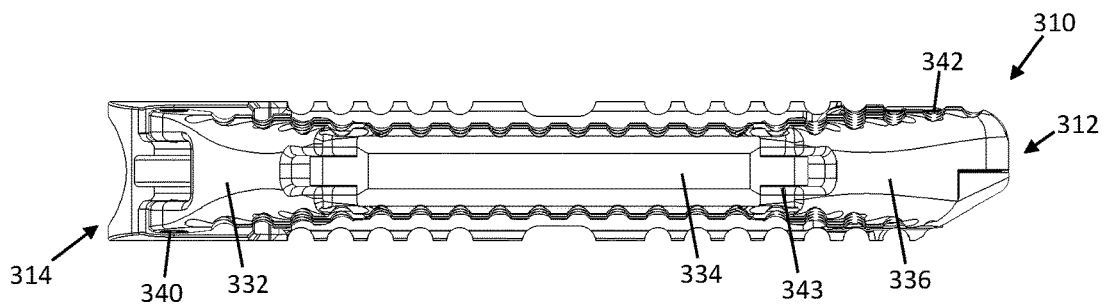
FIG. 28 is a posterior view of the expandable intervertebral implant of FIG. 24.

FIGS. 20-22 show the implant 210 according to the fourth embodiment in its fully expanded state. In addition to the features of the previously described embodiments, the anterior and posterior walls 230, 220 according to this embodiment are separated into an upper portion 220A, 230A and a lower portion 220B and 230B. During insertion and anterior unilateral expansion of the implant 210, the medial surfaces 217, 219 of the top and bottom portions of the anterior and posterior walls 230, 220 are in contact with each other upon full lateral expansion, the top portion 220A, 230A of the implant 210 is rotated about a pivot point 260 in the posterior wall 220 of the implant, causing the top portion 230A of the anterior wall to move away from the bottom portion 230B of the anterior wall. As best illustrated in FIG. 22, the displacement of the top portion 230 of the anterior wall results in the implant 210 having a greater height at the anterior wall 230 than at the posterior wall 220. In the exemplary embodiment shown in FIGS. 17-23, the top portion 230A of the implant 210 is displaced by movement of a ball linkage 267 from a lower pocket 261 to an upper pocket 263. The ball linkages 265, 267 are coupled to a tensioning element (not shown), such as a cable or wire, which is coupled to and capable of manipulation through the insertion tool (not shown). Once the implant 210 has achieved its full anterior expansion, the tensioning member is manipulated to cause the ball linkages 265, 267 to travel from the lower pocket 261 up the ramp until the balls of the ball linkage 265, 267 settle into the upper pocket 263. The movement of the ball linkage 265, 267 lifts the upper portion 230A of the implant 210 causing it to rotate about the pivot point 260 in the posterior wall 220 of the implant 210. Once the ball linkages 265 have settled in the upper pocket 263, the tension element is crimped to maintain the tension.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the invention is to cover all modifications, equivalents, and alternatives falling within the spirit and scope of the invention as defined herein.

What is claimed is:

1. An expandable intervertebral implant comprising:
a plurality of links coupled to one another by a plurality of hinges, each of said links comprising upper and lower portions; and
an expansion mechanism operatively connected to said links that moves said upper portion closer or further with respect to said lower portion, and wherein said upper and lower portions comprise a pivot point such that said upper portion moves non-parallel and/or non-symmetrically with respect to said lower portion,
wherein the expansion mechanism comprises a ball linkage and a pocket in the upper portion and a pocket in the lower portion, the pockets aligned to form a ball linkage pocket such that the ball linkage rests in the ball linkage pocket when the implant is in an unexpanded state, and wherein displacement of the ball linkage from the ball linkage pocket causes expansion of the implant.

2. The implant of claim 1, further comprising:
a telescoping first sidewall having a leading end and a trailing end and comprising a male portion received in a female portion;
a second sidewall having a leading end and a trailing end and comprising the plurality of links, the plurality of links including a first link, a second link and a third link, wherein the first link is coupled to the second link by a first hinge and the second link is coupled to the third link by a second hinge and wherein the leading end of the first sidewall is coupled to the leading end of the second sidewall by a third hinge and the trailing end of the first sidewall is coupled to the trailing end of the second sidewall by a fourth hinge, wherein a height of the second sidewall is greater than a height of the first sidewall after expansion of the upper portion; and
a locking element comprising a mating feature on the male portion of the first sidewall dimensioned to engage a mating feature on the female portion of the second sidewall.

3. The implant of claim 2, further comprising an insertion tool engaging aperture on the leading end of the first sidewall.

4. The implant of claim 1, further comprising anti-migration features on a top and bottom surface of the first and second side walls.

5. The implant of claim 1, further comprising a recessed portion in a central area of a top surface of the first sidewall to be used as a marker during radiographic techniques.

* * * * *